United States Patent [19]

Adahan

[11] Patent Number: 4,823,787
[45] Date of Patent: Apr. 25, 1989

[54] PORTABLE VENTILATOR APPARATUS

[76] Inventor: Carmeli Adahan, 1316/02 Ramot 03, Jerusalem 97 725, Israel

[21] Appl. No.: 71,327

[22] Filed: Jul. 9, 1987

[51] Int. Cl.⁴ .............................................. A61M 16/00
[52] U.S. Cl. ............................ 128/203.27; 128/205.18
[58] Field of Search ....................... 128/203.12, 203.26, 128/203.27, 204.17, 204.21, 205.18, 205.24

[56] References Cited

U.S. PATENT DOCUMENTS

| | | | |
|---|---|---|---|
| 3,499,601 | 3/1970 | Laerdal ................................ | 417/415 |
| 4,215,681 | 8/1980 | Zalkin et al. .................... | 128/204.21 |
| 4,699,137 | 10/1987 | Schroeder ....................... | 128/205.24 |

FOREIGN PATENT DOCUMENTS 116386  1/1970  Denmark ......................... 128/203.27

*Primary Examiner*—Gerald A. Michalsky
*Attorney, Agent, or Firm*—Benjamin J. Barish

[57] ABSTRACT

Portable ventilator apparatus, particularly useful for providing mechanical ventilation of a patient at home or during transport, comprises a pump unit and a separate humidifier unit and a separate fluid-collector unit selectively attachable to the pump unit. When the apparatus is to be used for mechanical ventilation, the pump unit, including a delivery tube, may be used alone or with the humidifier unit which is attached to the positive-pressure outlet of the pump unit; and when the apparatus is to be used for withdrawing fluid accumulating in the patient's lungs, the fluid-collector unit, including the delivery tube, is attached to the negative-pressure inlet of the pump unit. A solenoid valve controls the air pulses applied to the patient via the delivery tube to permit a wide variety of operations according to the particular situation.

14 Claims, 1 Drawing Sheet

PORTABLE VENTILATOR APPARATUS

BACKGROUND OF THE INVENTION

The present invention relates to ventilator apparatus, and particularly to portable ventilator apparatus useful for providing mechanical ventilation of a patient at home or during transport.

Ventilating apparatus is widely used for mechanically forcing air into the lungs of a patient requiring ventilatory assistance. Some ventilators are designed for continuous use in hospitals, such as in intensive care units; and others are designed as portable units for use in the home or during transport. Examples of the latter are described in U.S. Pat. Nos. 3,499,601, 4,215,681 and 4,493,614. The present invention is particularly applicable to ventilators of the portable type for use in the home or during transport.

Ventilators are usually also divided into the following types:

1. Pressure ventilators, usually including a source of compressed air administered by a solenoid valve at a rate of 10–30 breaths per minute. Such ventilators usually include large-size pistons (e.g., 10–12 inch diameters) having sealing surfaces with respect to the cylinders in which they move, and in general are characterized by bulky construction precluding portability, high power consumption because of continuous operation precluding the use of batteries, and/or poor control of the volume the patient inhales with each breath.

2. Volume ventilators, usually including a large reciprocating piston driven by an electric motor for compressing air into the patient's lungs at a preset fixed volume with the cycling frequency varying from 5 to 40 breaths per minute. Such ventilators are generally characterized by inability to attain high frequencies required for baby respiration, poor control of th volumes when they are set very low since the piston stroke becomes very critical, and/or poor mechanical efficiency since most of the energy is expended in overcoming friction in the piston seal and in the transmission from the motor to the piston.

3. Continuous positive airway pressure (CPAP) ventilators, usually including a compressor providing continuous positive pressure at a low pressure level. Such ventilators are usually used only for applying a positive pressure to the patient's lungs in order to help alleviate obstructive apnea during sleep while the patient breathes against the continuous pressure.

4. High-frequency positive-pressure ventilators, in which a source of compressed air is controlled to deliver air to the patient at controlled volumes and at rates between 60 and 120 breaths per minute. Such ventilators are usually of bulky construction and therefore are primarily used in clinical applications.

5. High-frequency jet ventilators, which include compressors delivering high pressure air directly to the lungs at frequencies of up to 400 cycles per minute.

6. High-frequency oscillation ventilators, which include compressors delivering very small volumes of pressurized air to the lungs at frequencies of up to 2400 cycles per minute.

An object of the present invention is to provide a novel ventilator apparatus which may be embodied in a compact, portable construction and which can substantially duplicate the performance of all six types of ventilators described above.

BRIEF SUMMARY OF THE INVENTION

According to the present invention, there is provided portable ventilator apparatus particularly useful for providing mechanical ventilation of a patient at home or during transport, comprising: a pump unit including a negative-pressure chamber having an inlet for drawing air into the chamber, and a positive-pressure chamber having an outlet for outletting pressurized air therefrom to the patient; a separate humidifier unit having a compartment for a humidifying liquid, an inlet into the compartment and connectable to the positive-pressure outlet of the pump unit, an outlet from the compartment, and a delivery tube connected to the latter outlet for delivering pressurized, humidified air to the patient; and a separate fluid collector unit including a first port connectable to the negative-pressure inlet of the pump unit, and a second port connectable to the patient's lungs for draining fluid accumulating therein.

According to another feature of the invention, the apparatus further comprises an exhalation valve assembly including a venting port for venting the delivery tube to the atmosphere, a valve member movable either to a closed position for disconnecting the delivery tube from the venting port to effect inhalation into the patient's lungs via the delivery tube, or to a closed position for disconnecting the delivery tube from the venting port to permit exhalation from the patient's lungs, and control means for controlling the valve member to control the inhalation and exhalation.

In the preferred embodiment of the invention described below, the control means comprises a fluid passageway from the positive-pressure chamber of the pump unit to the exhalation valve assembly, and a control valve in the passageway controlling the transmission of pressure from the positive-pressure chamber to the valve member in the exhalation valve assembly.

According to further features of the invention, the humidifier unit compartment includes a heater for heating the liquid therein and thereby controlling both the temperature and moisture content of the air supplied to the patient via the delivery tube; in addition, the heater is carried at the bottom of an insulating sleeve disposed within the compartment, the upper end of the insulating sleeve communicating with the inlet and outlet of the humidifier unit.

According to still further features of the invention, the pump unit comprises a cylinder; a pair of pistons reciprocated together within the cylinder; a pair of valve members carried by the pistons such as to produce a negative-pressure on the inner sides of the pistons, which inner sides define the negative-pressure chamber, and to produce a positive pressure on the outer sides of the pistons, which outer sides define two positive-pressure chambers, each of the latter chambers leading to an outlet from the pump unit for outletting pressurized air; the pump unit further includes a second pair of positive-pressure chambers each located between one of the first-mentioned positive-pressure chambers and the respective outlet from the pump unit, and a second pair of valve members controlling the flow of air from the first-mentioned positive-pressure chambers to the second pair of positive-pressure chambers.

In the described preferred embodiment, the pistons have a diameter of less than 5 cm, preferably 2.54 cm (1-inch), substantially smaller than the diameter (10–12 inches) commonly used in portable ventilators. The pump thus has a relatively small volume-displacement as compared to the relatively large volume-displacements of the pumps in the commonly used ventilators. Such a construction provides more accurate air metering, by controlling the reciprocating speed of the pistons, even when the pistons have a sealing-ring-free contact with the cylinder.

According to a still further feature, the pump unit includes an expansible bellows in the flow path of the air from the positive-pressure chamber to the delivery tube to damp oscillations in pressure produced by the reciprocating pistons.

As will be described more particularly below, ventilators may be built in accordance with the foregoing features providing both small, compact and lightweight construction for portability, and efficient, reliable, quiet and flexible operation enabling the apparatus to duplicate the performance of all of the above-described types of ventilators now in use.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF A PREFERRED EMBODIMENT

Overall Construction

Figure 1:
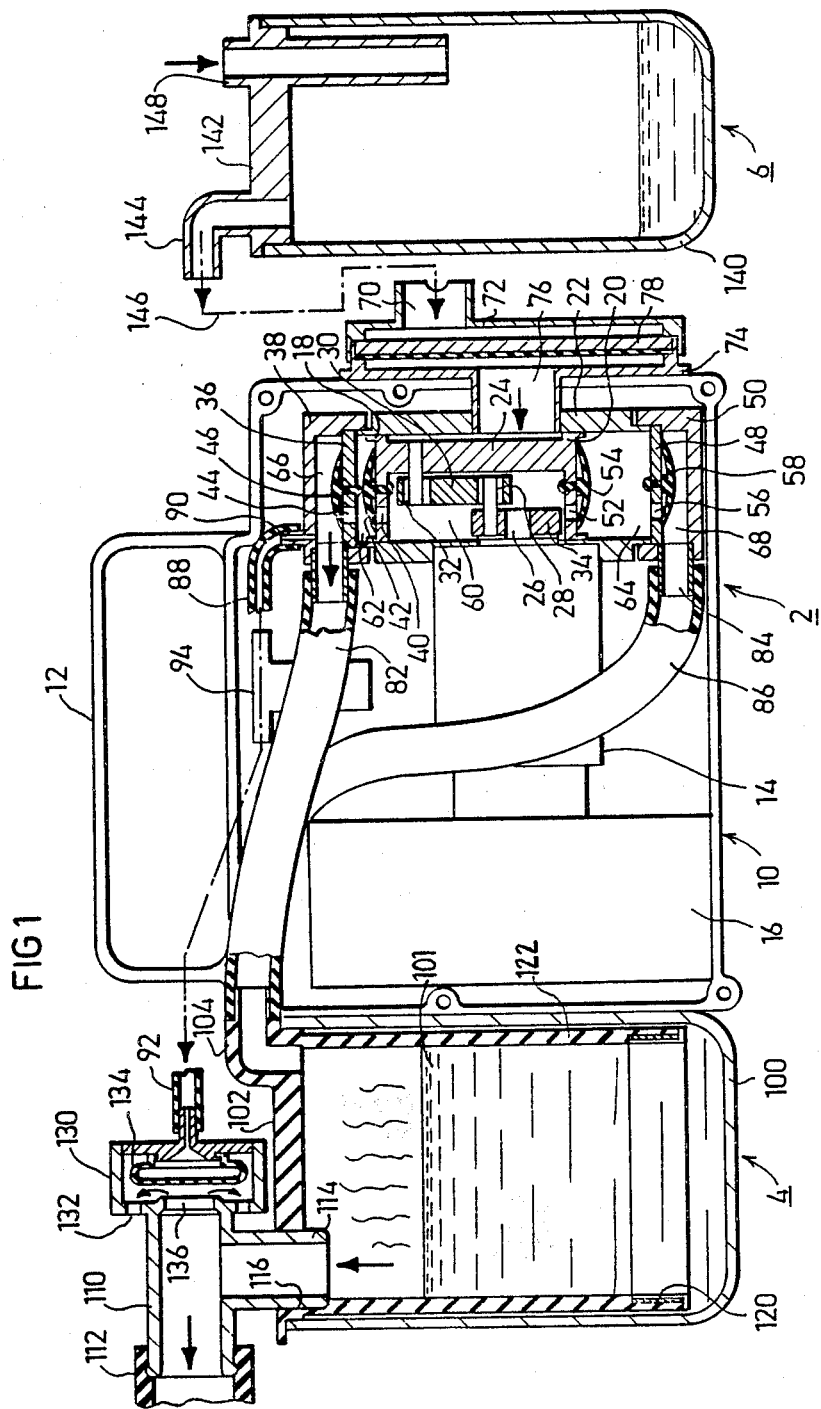
FIG. 1 is a longitudinal sectional view illustrating one form of ventilator apparatus constructed in accordance with the present invention.

The ventilator apparatus illustrated in FIG. 1 is designed to provide maximum portability. For this purpose, it is constituted of three separate units, namely a pump unit 2, a humidifier unit 4, and a fluid collector unit 6, which may be conveniently detached from each other for transportation or storage, and quickly attached to each other when the apparatus is to be used for providing mechanical ventilation.

Generally speaking, pump unit 2 includes the drive for producing the positive air pressure providing the mechanical ventilation; humidifier unit 4 is connectable to the positive-pressure outlet of the pump unit for humidifying the air outputted by that unit; and fluid collector unit 6 is connectable to the negative-pressure inlet of the pump unit, whenever desired, in order to draw fluid accumulating in the lungs of the patient. Each of these units will be described more particularly below.

Pump Unit 2

Pump unit 2 includes a housing 10 provided with a handle 12 for portability, an electric motor 14 for driving the pump, and a compartment 16 for a self-contained power supply. Motor 14 drives a pair of pistons 18, 20 disposed within a cylinder 22 and connected together by a piston rod 24. Motor 14 is a rotary motor and its output rotary shaft 26 is coupled to piston rod 24 via an eccentric bearing 28, a crank arm 30, and another eccentric bearing 32, so that the rotary output of the motor is converted to a reciprocatory movement of the two pistons 18, 20 within the cylinder 22. The rotary shaft 26 of the motor further includes a flywheel 34.

The end of cylinder 22 adjacent to piston 18 is closed by an end wall 36 fixed to the cylinder by an end fitting 38. Piston 18 is formed with a port 40 closed by an umbrella-type valve 42 disposed on the outer face of the piston to permit air to flow outwardly through port 40 but not in the reverse direction. End wall 36 is similarly formed with a port 44 closed by another umbrella-type valve 46 on the outer face of the end wall to permit air to flow outwardly through port 44 and not in the reverse direction. A similar construction is provided at the opposite end of cylinder 22 adjacent to piston 20, namely an end wall 48 fixed by an end fitting 50, a port 52 through piston 20 closed by an umbrella-type valve 54 on the outer face of the piston, and a port 56 through end wall 48 and closed by an umbrella-type valve 58 on the outer face of the end wall.

It will thus be seen that the space on the inner sides of the two pistons 18, 20 defines a common chamber 60 in which a negative pressure is produced during the reciprocation of the two pistons, and that the spaces on the outer sides of the two pistons define two chambers 62, 64 in which a positive pressure is produced during the reciprocation of the pistons. It will also be seen that the spaces 66 and 68 between the end walls 36 and 48 and their respective end fittings 38 and 50 define two further positive-pressure chambers communicating with the positive-pressure chambers 62 and 64, respectively, through ports 44 and 56 of their respective end walls.

The air drawn into the negative-pressure chamber 60 during the reciprocation of the pistons 18, 20 enters the chamber via an inlet 70 formed in an inlet fitting 72. The latter fitting is removably attached to an annular flange 74 formed in housing 10 around an inlet port 76 communicating with the negative-pressure chamber 60. A filter 78 is interposed between fitting 72 and flange 74 to filter the air inletted into the negative-pressure chamber 60.

The positive-pressure chamber 66 at the piston 18 end of the cylinder 22 includes an outlet fitting 80 adapted to receive a tube 82 for outletting the positive-pressure air produced at that end of the pump; and positive-pressure chamber 68 at the opposite end of the cylinder similarly includes an outlet fitting 84 receiving a tube 86 for outletting the positive-pressure air produced at that end of the pump. The positive-pressure air produced in chamber 66 is further outputted, via a tube 88 secured to a nipple 90 formed in end fitting 38, to another tube 92 for control purposes. The positive-pressure air outputted via tubes 88 and 92 is controlled by a solenoid valve 94, for control purposes as to be described more particularly below.

Humidifier Unit 4

The humidifier unit 4 is in the form of a container 100 for receiving a supply of water 101 to humidify the positive-pressure air outputted by pump unit 2. The upper end of container 100 is closed by a top wall 102 having an inlet T-fitting 104 attachable to the two tubes 82, 86 outletting the positive-pressure air from the two output ends of the pump unit 2.

The humidifier unit 4 further includes an outlet fitting 110, attachable to the top wall 102 of container 100, for receiving a delivery tube 112 to deliver the humidified air to the patient. Delivery tube 112, which may be of any known construction, generally includes a mask (not shown) attachable over the mouth of the patient to receive the mechanical ventilation provided by the illustrated apparatus. Outlet fitting 110 is formed with a connector 114 receivable within an output port 116 formed in the top wall 102 of the humidifier container 100.

The humidifier unit 4 further includes a heater 120 in the form of an electrical coil carried at the lower end of an insulating sleeve 122. Electrical heater 120 is disposed so as to be completely immersed in the water within the humidifier container 100, and thereby to heat the water enclosed within sleeve 122. The open end of sleeve 122 is aligned with the inlet fitting 104 and with the outlet port 116, so that the air passing through the humidifier to the delivery tube 112 is humidified by the water 101 within sleeve 122 and heated by heater 120.

Sleeve 122 is made of plastic insulating material to conserve the heat of the water within the sleeve. The humidifier container 100 is of rectangular configuration, and the sleeve 122 is of cylindrical configuration having an outer diameter which is substantially less than the length of the humidifier container, e.g., substantially equal to its width as shown in FIG. 1, so as to occupy a fraction of the complete volume of the container. This arrangement thus concentrates the heat produced by its heater 120 to the portion of the water brought into direct contact with the air passing through the humidifier unit, and thereby decreases the power required for heating the water.

Outlet fitting 110 further includes an exhalation valve assembly, generally designated 130, for controlling the exhalation of the patient. Thus, the exhalation valve assembly 130 includes one or more (two being shown in FIG. 1) venting ports 132 for venting the delivery tube 112 to the atmosphere, and a valve member 134, in the form of a mushroom valve, movable either to an open position (shown in FIG. 1) or to a closed position with respect to a valve opening 136 formed in assembly 130.

Mushroom valve 134 is controlled by the pressure applied thereto from the positive-pressure chamber 66 via solenoid valve 94 and tube 92. Normally, mushroom valve 134 is in its open position as illustrated in FIG. 1, thereby establishing communication between delivery tube 112 and venting ports 132, to permit exhalation by the patient to the atmosphere via the latter venting ports; however, when a positive pressure is transmitted to the exhalation valve assembly 130 via tube 92, under the control of solenoid valve 94, mushroom valve 134 moves to its closed position with respect to valve opening 136. This blocks communication between delivery tube 112 and the venting ports 132, and thereby effects inhalation into the patient's lungs by the positive pressure of the air passing through tubes 82, 86, humidifier 100, and delivery tube 112.

Fluid Collector Unit 6

The fluid collector unit 6 is attachable to the negative-pressure inlet connector 70 of the pump unit 2 whenever it is desired to withdraw fluids accumulating in the lungs of the patient. Thus, collector unit 6 includes a container 140 closed at its upper end by a top wall 142 formed with, a fitting 144 connectable by a tube, shown schematically at 146, to the negative-pressure inlet 70 of pump unit 2, and with a further coupling 148 adapted to receive another tube, e.g., a catheter tube insertable into the lungs of the patient. Thus, when the fluid collector unit 6 is connected to the negative-pressure inlet 70 of the pump unit 2, the negative pressure produced by the pump unit draws out of the patient's lungs any fluid therein, which fluid is accumulated in container 140.

Overall Use and Operation

Normally the humidifier unit 4 and the fluid collector unit 6 may be detached from the pump unit 2 so as to permit convenient portability and storage of the apparatus.

When the apparatus is to be used for providing mechanical ventilation of a patient, the humidifier unit 4 is attached to the pump unit 2, and the electric motor 14 is energized to produce positive-pressure air passing through the two outlet tubes 82, 86, via the humidifier unit 4, to the delivery tube 112 attached to the patient. The operation of motor 14 reciprocates the two pistons 18, 20 within cylinder 22, to pump the air from the positive-pressure chambers 62, 66 and 64, 68 at the opposite ends of cylinder 22, via their respective tubes 82, 86 into the humidifier unit 100, where the air is humidified by the water heated by the electrical heating element 120 before passing to the delivery tube 112.

The positive-pressure air thus applied to the delivery tube 112 is controlled by solenoid valve 94 and the exhalation valve assembly 130. Thus, whenever solenoid valve 94 is open, the positive-pressure in chamber 66 is applied via tube 92 to mushroom valve 134 to close valve opening 136, and thereby to effect inhalation of the air outletted from the pump unit 2 via tubes 82, 86 and humidifier unit 4 to the delivery tube 112; and when solenoid valve 94 is closed, mushroom valve 134 opens its valve opening 136 to establish communication between delivery tube 112 and the venting ports 132 to permit exhalation to the atmosphere by the patient.

It will thus be seen that a high degree of control may be effected merely be controlling solenoid valve 94 and also by controlling the speed of rotation of motor 14. During exhalation, the motor is turned off.

Further, the moisture content, and also the temperature, of the humidified air may be conveniently controlled by controlling electrical heater 120.

In emergencies, the pump unit 2 may be used alone, i.e., without the humidifier unit 4.

Whenever it is desired to withdraw fluids from the patient's lungs, the humidifier unit 4 is disconnected from the positive-pressure side of pump unit 2, and the fluid collector unit 6 is connected to the negative-pressure inlet 70. In addition, a catheter tube is applied to the inlet coupling 148 of the fluid collector unit 6, so that the negative pressure produced by the pump unit 2 is now applied to the patient's lungs via the catheter tube thereby drawing out fluid collected therein into the fluid collector unit 6.

Figure 3:
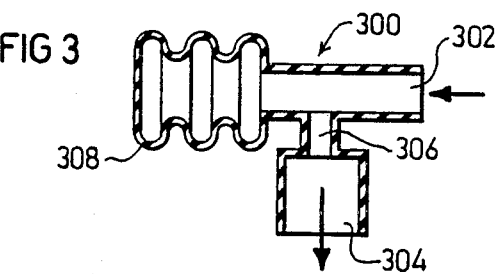
FIG. 3 is a fragmentary view illustrating a variation that may be used in the construction of one or more of the flow passageways in the ventilator apparatus of FIG. 1.

The Variation of FIG. 3

Figure 2:
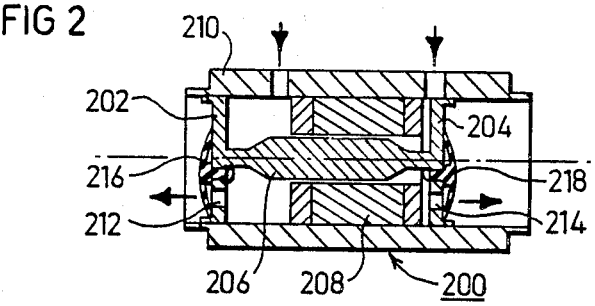
FIG. 2 is a fragmentary view illustrating a variation that may be used in the drive.

FIG. 2 illustrates a solenoid drive, generally designated 200, which may be used in place of the rotary-motor drive 14 in FIG. 1. Thus, the solenoid drive 200 in FIG. 2 comprises a pair of pistons 202, 204 connected together by an armature 206 received within an electrical coil 208, such that energization of the coil reciprocates the two pistons within a cylinder 210. The two pistons 202, 204 include ports 212, 214 closed by umbrella valves 216, 218, respectively, for producing a negative-pressure on the inner sides of the pistons, and a positive pressure on the outer sides, as described above with respect to FIG. 1. The remainder of the structure of the pump unit, and the operation of the pump unit as well as of the remainder of the apparatus, is the same as described above with respect to FIG. 1.

Variation of FIG. 3

FIG. 3 illustrates a variation in the construction of the flow path in order to damp the pulses generated by the reciprocating pistons. For example, the coupling illustrated in FIG. 3 could be applied between the outlet fittings 80, 84 and their outlet tubes 82, 86, and/or between the outlet coupling 110 and the delivery tube 112.

Thus, the coupling illustrated in FIG. 3, therein generally designated 300, comprises an air inlet 302 (e.g., coupled to outlet fitting 110), an air outlet 304 (e.g., coupled to the delivery tube 112) and a communicating orifice 306 between the two couplings. Inlet coupling 302 further includes an expansible, flexible bellows 308 just upstream of orifice 306, which tends to smooth out the air flow from the air inlet 302 to the air outlet 304.

It will be appreciated that many other variations, modifications and applications of the invention may be made.

What is claimed is:

1. Portable ventilator apparatus particularly useful for providing mechanical ventilation of a patient at home or during transport, comprising:
   a pump unit including a negative-pressure chamber having an inlet for drawing air into the chamber, and a positive-pressure chamber having an outlet for outletting pressurized air therefrom to the patient; said pump unit including a pair of reciprocating pistons each of a diameter of less than 5 cm, and a drive for driving said pistons through reciprocatory cycles, whereby there is produced a relatively low volume-displacement during each reciprocatory cycle;
   a separate humidifier unit having a compartment for a humidifying liquid, an inlet into said compartment and connectable to the positive-pressure outlet of the pump unit, an outlet from said compartment, and a delivery tube connected to said latter outlet for delivering pressurized, humidified air to the patient;
   a separate fluid collector unit including a first port connectable to the negative-pressure inlet of the pump unit, and a second port connectable to the patient's lungs for draining fluid accumulating therein;
   an exhalation valve assembly including a venting port for venting the delivery tube to the atmosphere, a valve member movable either to a closed position for disconnecting said delivery tube from said ventilating port to effect inhalation into the patient's lungs via said delivery tube, or to an open position for connecting said delivery tube to said ventilating port to permit exhalation from the patient's lungs; and control means for controlling said valve member to control said inhalation and exhalation.

2. The apparatus according to claim 1, wherein said control means comprises a fluid passageway from the positive-pressure chamber of the pump unit to said exhalation valve assembly, and a solenoid control valve in said passageway controlling the transmission of pressure from the positive-pressure chamber to the valve member in the exhalation valve assembly.

3. The apparatus according to claim 1, wherein said humidifier unit compartment includes a heater for heating the liquid therein and thereby controlling both the temperature and moisture content of the air supplied to the patient via the delivery tube.

4. The apparatus according to claim 1, wherein said pump unit comprises: a common cylinder for said pair of pistons ; a pair of valve members carried by said pistons such as to produce a negative-pressure on the inner sides of said pistons, which inner sides define said negative-pressure chamber, and to produce a positive pressure on the outer sides of said pistons, which outer sides define two positive-pressure chambers, each of the latter chambers leading to an outlet from the pump unit for outletting pressurized air.

5. The apparatus according to claim 4, wherein said pump unit includes a second pair of positive-pressure chambers each located between one of the first-mentioned positive-pressure chambers and the respective outlet from the pump unit, and a second pair of valve members controlling the flow of air from the first-mentioned positive-pressure chambers to said second pair of positive-pressure chambers.

6. The apparatus according to claim 5, wherein all said valve members are umbrella valves.

7. The apparatus according to claim 4, wherein said pistons are in sealing-ring-free contact with the cylinder.

8. The apparatus according to claim 4, wherein said pair of pistons are reciprocated together by a rotary motor via an eccentric crank.

9. The apparatus according to claim 4, wherein said pump unit includes an expansible bellows in the flow path of the air from the positive-pressure chamber to the delivery tube to damp oscillations in pressure produced by the reciprocating pistons.

10. Ventilator apparatus comprising:
    a cylinder;
    a pair of pistons reciprocated together within said cylinder by an electric motor driving said pistons through reciprocatory cycles, each of said pistons having a diameter of less than 5 cm whereby there is produced a relatively low volume-displacement during each reciprocatory cycle;
    a pair of valve members carried by said pistons such as to produce a common negative-pressure chamber on one side of said pistons, and two positive-pressure chambers on the other side of said pistons when the pistons are reciprocated within said cylinder;
    each of said positive-pressure chambers including an outlet for outletting pressurized air;
    a delivery tube connectable to said outlets from the positive-pressure chambers;
    an exhalation valve assembly including a venting port for venting the delivery tube to the atmosphere, and a valve member movable either to a closed position for disconnecting said delivery tube from said ventilating port to effect inhalation via said delivery tube, or to an open position for connecting said delivery tube to said ventilating port to permit exhalation;
    and control means for controlling said valve member to control said inhalation and exhalation.

11. The apparatus according to claim 10, wherein said pistons are in sealing-ring-free contact with the cylinder.

12. The apparatus according to claim 10, wherein said control means comprises a fluid passageway from the positive-pressure chambers of the pistons to said exhalation valve assembly, and a control valve in said passageway controlling the transmission of pressure from the positive-pressure chamber to the valve member in the exhalation valve assembly.

13. The apparatus according to claim 10, further including an expansible bellows in the flow path of the air from the positive-pressure chambers to the delivery tube to damp oscillations in pressure produced by the reciprocating pistons.

14. The apparatus according to claim 10, further including a separate fluid collector unit having a first port connectable to the negative-pressure chambers of the pistons, and a second port connectable to the patient's lungs for draining fluid accumulated therein.

* * * * *